(12) United States Patent
Littich

(10) Patent No.: US 10,100,828 B2
(45) Date of Patent: Oct. 16, 2018

(54) SYSTEMS AND METHODS FOR ANALYZING AN INFUSION PUMP

(71) Applicant: LLOYD INDUSTRIES, INC., St. Charles, MO (US)

(72) Inventor: Aaron Littich, O'Fallon, MO (US)

(73) Assignee: LLOYD INDUSTRIES, INC., St. Charles, MO (US)

( * ) Notice: Subject to any disclaimer, the term of this patent is extended or adjusted under 35 U.S.C. 154(b) by 34 days.

(21) Appl. No.: 15/486,729

(22) Filed: Apr. 13, 2017

(65) Prior Publication Data
US 2017/0298929 A1 Oct. 19, 2017

Related U.S. Application Data

(60) Provisional application No. 62/322,033, filed on Apr. 13, 2016.

(51) Int. Cl.
| | |
|---|---|
| *F04B 51/00* | (2006.01) |
| *F04B 1/02* | (2006.01) |
| *F16K 31/04* | (2006.01) |
| *A61M 5/142* | (2006.01) |
| *A61M 5/168* | (2006.01) |
| *F04B 53/10* | (2006.01) |

(52) U.S. Cl.
CPC ......... *F04B 51/00* (2013.01); *A61M 5/14216* (2013.01); *A61M 5/16831* (2013.01); *F04B 1/02* (2013.01); *F04B 53/10* (2013.01); *A61M 2005/16863* (2013.01); *A61M 2205/18* (2013.01); *A61M 2205/3331* (2013.01); *A61M 2205/3337* (2013.01); *A61M 2205/50* (2013.01); *A61M 2205/52* (2013.01); *A61M 2205/70* (2013.01); *F16K 31/04* (2013.01)

(58) Field of Classification Search
CPC .. F04B 51/00; F04B 1/02; F04B 53/10; F16K 31/04; A61M 5/14216; A61M 5/16831; A61M 2005/16863; A61M 2205/18; A61M 2205/3331; A61M 2205/3337; A61M 2205/50; A61M 2205/52; A61M 2205/70
See application file for complete search history.

(56) References Cited

U.S. PATENT DOCUMENTS

| | | | | |
|---|---|---|---|---|
| 4,468,222 A | * | 8/1984 | Lundquist | ......... A61M 5/14216 417/236 |
| 4,715,959 A | * | 12/1987 | Allan | ...................... A61M 1/16 210/321.71 |
| 5,336,053 A | * | 8/1994 | Wynkoop | .......... A61M 5/16854 417/53 |
| 5,695,473 A | * | 12/1997 | Olsen | ................ A61M 5/16859 604/153 |
| 5,843,022 A | * | 12/1998 | Willard | ................... A61M 1/00 604/30 |

(Continued)

*Primary Examiner* — David Bolduc
(74) *Attorney, Agent, or Firm* — Barta, Jones & Foley, P.C.

(57) ABSTRACT

Systems and methods for analyzing an infusion pump are provided. One infusion pump analyzer includes a fluid flow path configured to be coupled to an infusion pump to be tested and a pair of fluid chambers. The infusion pump analyzer further includes dual linear piston pumps coupled with the pair of fluid chambers and the fluid flow path to control the flow of fluid therethrough, and a valve coupled with the pair of fluid chambers and configured to rotate to selectively fill and drain the pair of fluid chambers.

11 Claims, 14 Drawing Sheets

(56) References Cited

U.S. PATENT DOCUMENTS

| | | | | |
|---|---|---|---|---|
| 5,935,099 A | * | 8/1999 | Peterson | G09B 19/003 |
| | | | | 604/65 |
| 2002/0004645 A1 | * | 1/2002 | Carlisle | A61M 5/14224 |
| | | | | 604/151 |
| 2010/0286614 A1 | * | 11/2010 | Ring | A61M 5/14276 |
| | | | | 604/152 |
| 2012/0053557 A1 | * | 3/2012 | Abal | A61M 5/1413 |
| | | | | 604/500 |
| 2013/0177455 A1 | * | 7/2013 | Kamen | G06F 19/3418 |
| | | | | 417/313 |
| 2013/0261599 A1 | * | 10/2013 | Haueter | A61M 5/14216 |
| | | | | 604/506 |
| 2013/0336814 A1 | * | 12/2013 | Kamen | A61M 5/16859 |
| | | | | 417/282 |
| 2014/0257097 A1 | * | 9/2014 | Bonnette | A61M 5/007 |
| | | | | 600/432 |
| 2014/0350510 A1 | * | 11/2014 | Carlisle | A61M 5/155 |
| | | | | 604/500 |
| 2015/0064036 A1 | * | 3/2015 | Eberhard | F04B 53/16 |
| | | | | 417/557 |
| 2016/0108906 A1 | * | 4/2016 | Wichmann | F04B 51/00 |
| | | | | 73/168 |

* cited by examiner

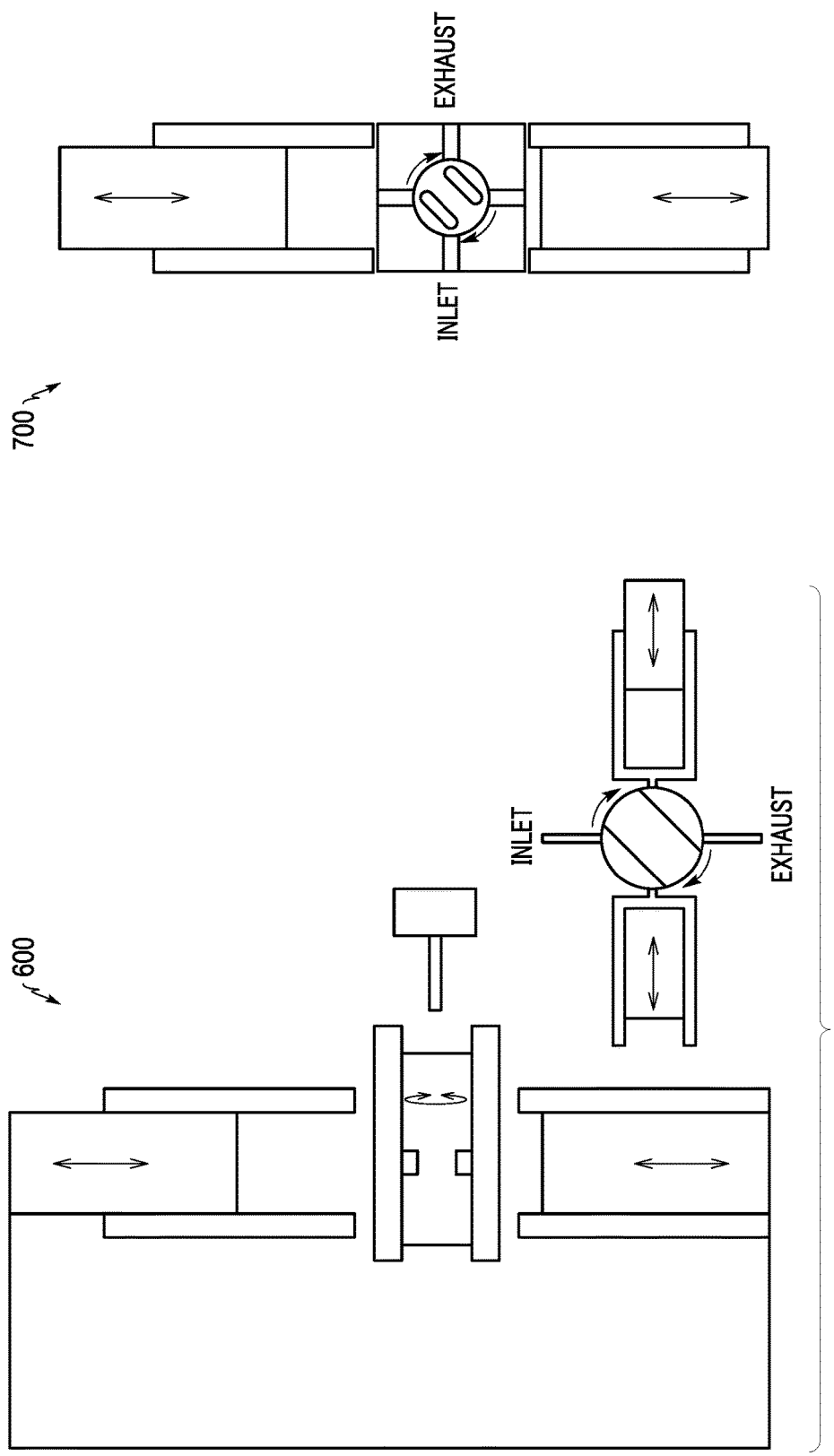

SYSTEMS AND METHODS FOR ANALYZING AN INFUSION PUMP

CROSS-REFERENCE TO RELATED APPLICATIONS

This nonprovisional application claims the benefit of and priority to U.S. Provisional Application No. 62/322,033, filed Apr. 13, 2016. The disclosure of the prior application is hereby incorporated by reference herein in its entirety.

BACKGROUND

Medical devices may be used to deliver fluids, medications and/or nutrients into a patient's body in a controlled manner. For example, infusion pumps are commonly used devices that dispense a programmable volume and flow rate of medical fluids into patients. Infusion pumps must be tested on a periodic basis to ensure that the devices are functioning safely and accurately. The safety and performance indicators tested may include flow rate, volume delivered, and occlusion pressure.

In normal operation, a delivery volume and flow rate of infusion pumps are set by the user or clinical technician. Typical volumes range from 1 mL to 1000 mL, at flow rates of 0.1 mL/hr to 1000 mL/hr. Typical infusion rates are generally in the 100 to 200 mL/hr range. Infusion pumps are required to have a safety feature that detects soft occlusions (restrictions which elevate infusion pressure) as well as hard occlusions (blockage) downstream in the administration set. When detected, in conventional infusion pumps, these events cause an audible alarm and/or other signal to be sent to the clinician or user. In the case of a hard occlusion, the infusion pump stops pumping fluids. This feature is very important because several unsafe outcomes can result if the infusion pump continues to pump when an occlusion exists, such as bursting of the administration set due to overpressure, interruption of vital fluids or drugs to the patient, and dangerous sudden-flow conditions when the occlusion is cleared without alarm. Due to the compliance of the tubing in the administration set, extra volume known as a bolus can build up between the infusion pump and patient administration site upon an occlusion event. In some cases, this bolus volume can be potentially dangerous to the patient if the occlusion (blockage) is removed as it will suddenly be infused into the body. Certain drugs may be dangerous if the infusion rate is suddenly increased in such a manner, especially in pediatric or infant patients. Many pumps now include an auto-backup function that reverses the infusion pump to clear this bolus volume upon hard occlusion.

There are several conventional techniques and devices used for administering the safety and performance tests of infusion pumps. Some basic techniques for testing volume delivered include the use of calibrated graduated cylinders, burettes, or electronic balances. In the case of the electronic balance, the volume is indirectly measured by measuring the mass of the dispensed fluid and then calculating its volume based on the fluid's density. Average flow rates are measured via a stopwatch in tandem with one of the above volume measurement devices. The flow rate is measured by taking the volume over the time measured between flow start and conclusion. For measuring occlusion pressure, pressure gauges or meters are typically used.

While these devices may inherently be considered accurate, they can be affected by user error or judgment. As an example, in the case of the graduated cylinder or burette, readability of the fluid level against a scale graduation can be greatly impacted by the user and technique. Another example of potential difficulty is fluid evaporation in electronic balance method, which can be overcome, but presents additional complexity and sources of error. Additionally, these methods can be very time consuming and have inherent limitations, such as the inability to measure instantaneous flow.

Several devices have been designed over the years to incorporate and improve these manual methods into more automated electronic systems. These systems are commonly known as infusion pump analyzers. Some of these even combine testing functions, such as volume/flow measurement plus occlusion pressure measurement. These devices vary greatly in measurement techniques used in their designs. These techniques generally include electronic burette systems, injected bubble tracking systems and fluid metering pumps. Electronic burette systems use a series of photosensors installed along a precision glass tube to measure volume and flow. These systems use an electronically actuated valve to alternate the fluid path to the burette between intake and exhaust ports so that it can dump the previous volume sample and get ready for the next. A pressure sensor is located before the valve in the intake port to measure fluid pressure and for occlusion testing.

Injected bubble systems use a similar electronic burette design, except that these systems locate the glass tube horizontally and intentionally inject an air bubble into the incoming fluid stream to measure the volume and flow rate. These systems require several valves, in addition to the mechanicals required to create the air bubble.

Fluid metering pumps use a pump mechanism to meter or measure the volume. These pumps have a pressure sensor on the inlet side to sense the incoming pressure, which is also used for occlusion pressure measurement. During flow and volume testing, the pressure sensor reading is used to control the pump speed so that the net pressure is nulled. This system requires no valves as the valve is built in to the pump itself.

Each of these systems has related strengths and weaknesses. For example, electronic burette and injected bubble designs can be fouled by improper fluids such as salines or glucose solutions. These can build up a film on the inside of the glass walls, disrupting the ability of the photosensors to measure the fluid. Additionally, these systems are prone to measurement inaccuracy or disruption by air bubbles, which may require complete reset of the test being undertaken. Typically manufacturers specify specially prepared test solutions containing purified water (e.g., deionized water) and a surfactant (1% micro-90 cleaning solution) to ensure valid tests. The surfactant is recommended to be used to keep the glass walls clean. Both systems have to be well primed and clear of bubbles before testing can begin. Both systems are delicate due to the special glass assemblies which require great care in handling and transport. In addition, some test procedures and specifications require the ability for the infusion test to be done at varying pressure conditions (backpressure or vacuum) to test additional pump safety functions. These systems do not have the ability to generate this backpressure or vacuum due to their passive design, and thus require these pressures be generated externally by the technician.

Fluid metering pump designs are vastly different as these designs are not sensitive to bubbles, and can easily generate a backpressure or vacuum. However, these pump designs are usually very costly due to the specialized materials used for construction such as precision machined ceramics. The conventional design uses a piston that directly acts within a bore or liner. The piston is actuated with an offset drive mechanism that is adjusted or calibrated for volume pump cycle, which is generally fixed somewhere around 50 uL per motor revolution. This design is simple in that the design only requires one motor to achieve two mechanical motions that would typically require respective actuators. However, the design requires significant actuation power, and like the electronic burette system, occludes (blocks) the inlet port while evacuating or exhausting the last sample. This temporary partial occlusion is an occlusion also of the infusion device under test (DUT), which can actually impact infusion pump operation. However, this effect may lead to potentially inaccurate or unrealistic flow parameters (as compared to infusion into an actual patient) due to the temporary but reoccurring pressure interruptions. Another potential weakness in a typical fluid metering design relates to the fixed cycle volume. If graphed over angular position of the actuating motor, the pump volume or displacement would appear sinusoidal. Thus, to resolve sub-cycle volumes (under 50 uL for example above), the angular position of the motor has to be well regulated and the cycle volume versus angular relationship well parameterized and constant.

Thus, current technology infusion pump analyzers for testing infusion pumps may not adequately and/or accurately perform the specified tests, and can be sensitive to setup and operation.

SUMMARY

In one embodiment, an infusion pump analyzer is provided that includes a fluid flow path configured to be coupled to an infusion pump to be tested and a pair of fluid chambers. The infusion pump analyzer further includes dual linear piston pumps coupled with the pair of fluid chambers and the fluid flow path to control the flow of fluid therethrough, and a valve coupled with the pair of fluid chambers and configured to rotate to selectively fill and drain the pair of fluid chambers.

In another embodiment, a method of controlling fluid metering for an infusion pump analyzer is provided. The method includes starting linear motion of dual linear pistons in a first linear direction to drain one fluid chamber and fill another fluid chamber through passageways aligned with openings in a valve and then stopping linear motion of the dual linear pumps when the draining and filling that define exhaust and intake phases, respectively, are completed. The method further includes performing a valve cycle that causes a portion of the valve to rotate in a first direction to align the passageways with a different respective pair of openings and stopping the valve cycle, such that rotation of the valve is stopped. The method also includes starting linear motion of the dual linear pistons in a second linear direction, the second linear direction being opposite to the first linear direction that caused filling and draining of the fluid chambers that were drained and filled, respectively, when the dual linear pistons were moved in the first linear direction. The method additionally includes stopping linear motion of the dual linear pumps when the draining and filling that define exhaust and intake phases, respectively, are completed. The method also includes performing a valve cycle that causes a portion of the valve to rotate in a second direction to align the passageways with a different respective pair of openings, the second direction being opposite to the first direction, and stopping the valve cycle, such that rotation of the valve is stopped.

BRIEF DESCRIPTION OF THE DRAWINGS

FIGS. 17A-17E illustrate analyzer configurations in accordance with various embodiments.

DETAILED DESCRIPTION OF THE EMBODIMENTS

Figure 1:
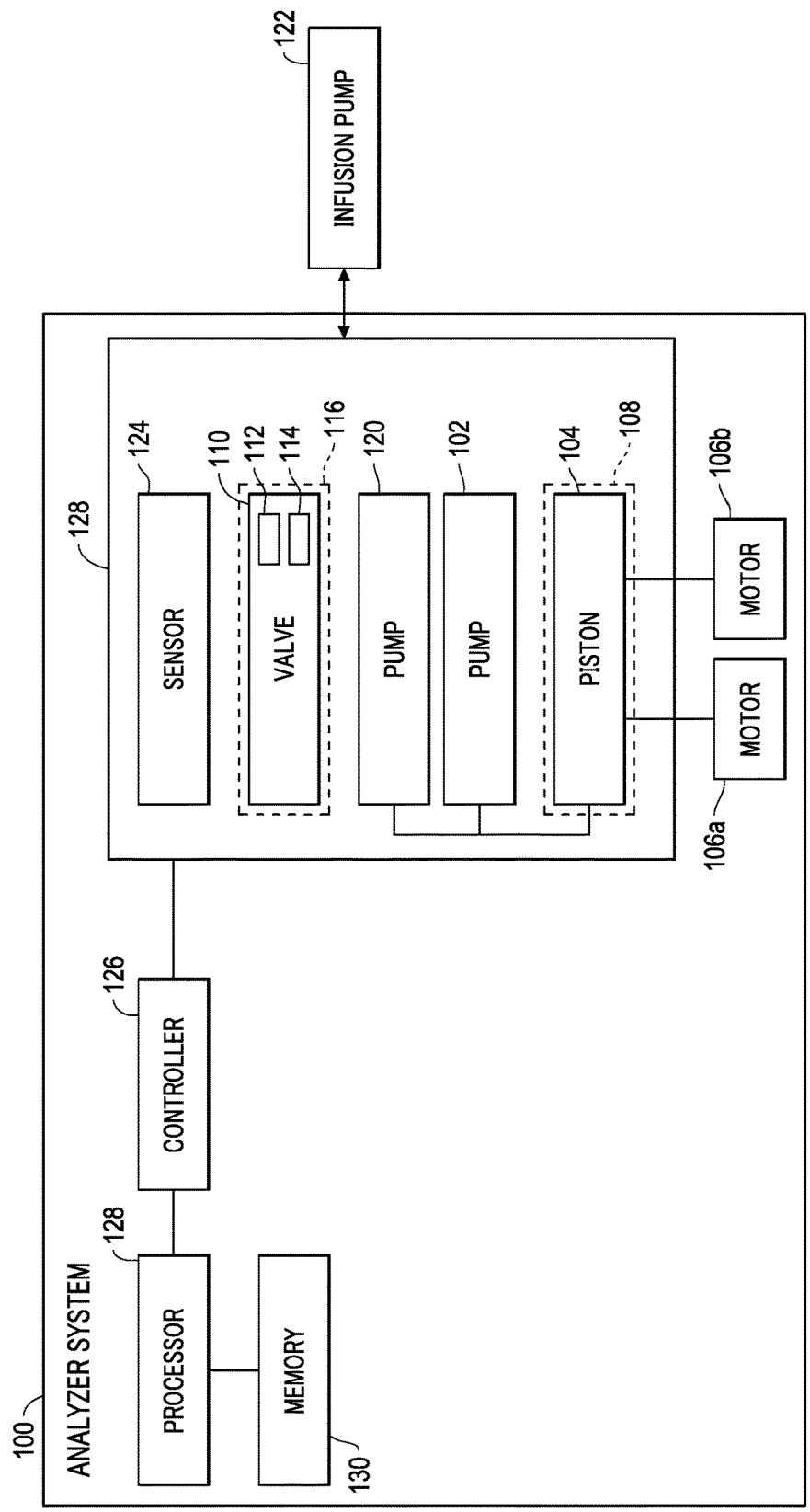
FIG. 1 is a block diagram of an analyzer system in accordance with one embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry, between software elements or between hardware and software implementations. Thus, for example, one or more of the functional blocks may be implemented in a single piece of hardware or multiple pieces of hardware. Similarly, the software programs may be stand-alone programs, may be incorporated as subroutines in an operating system, may be implemented in a field-programmable gate array, and the like. It should be understood that the various embodiments are not limited to the arrangements and instrumentality shown in the drawings.

As used herein, the terms "system," "subsystem," "unit," or "module" may include any combination of hardware and/or software system that operates to perform one or more functions. For example, a system, subsystem, unit, or module may include a computer processor, controller, or other logic-based device that performs operations based on instructions stored on a tangible and non-transitory computer readable storage medium, such as a computer memory. Alternatively, a system, subsystem, unit, or module may include a hard-wired device that performs operations based on hard-wired logic of the device. The systems, subsystems, modules, or units shown in the attached figures may represent the hardware that operates based on software or hard-wired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for testing medical equipment, which in various embodiments includes infusion pumps. The various embodiments may be used, for example, to calibrate and/or perform routine performance verification of infusion pumps. It should be noted that although various embodiments may be described in connection with testing particular infusion pumps, the various embodiments may be used to test different types of devices for use in various different applications. Additionally, while various embodiments may be described in connection with testing the operation of an infusion pump with respect to particular operating characteristics, such as particular volume and delivery requirements, the various embodiments may be used to test different operating characteristics.

Various embodiments are programmable to allow for testing of different operating characteristics, such as different flow rates, delivery volumes, and occlusion pressures. For example, one or more embodiments may be configured to test one or more different operating characteristics or requirements for the infusion pumps.

One or more embodiments provide systems and methods for testing infusion pumps using alternate fluid metering pump designs. In some embodiments, the analyzer or testing system 100, such as shown in FIG. 1, includes a pump 102, such as a fluid metering pump that includes a ceramic piston 104 directly acting within a ceramic liner or cylinder, which are machined together as a set with very close tolerances. The direct-acting design includes no seals or piston cups used to perform the pumping. The end of the piston 104 may be machined with a flat to perform rotational valving in various embodiments, while in other embodiments, there is no flat machined.

Conventional fluid metering devices only allow for fixed volume metering/dispensing of a preset full cycle volume (typically 50 μL) or control the rotational angle of the actuating motor so as to resolve smaller volumes within the full cycle. However, unlike various embodiments described herein that provide more accurate and controllable sub-cycle volume measurements, these conventional fluid metering devices have accuracy issues because of the way positional control, or positional feedback (lack thereof) is implemented, which relies on the open-loop position control of the motor. This is because the only position monitored in conventional devices is the starting position of the pump cycle, which means that several multiples of a full pump cycle volume (e.g., 50 uL) must be metered before any level of accuracy is developed. Various embodiments provide more accurate testing that do not suffer from these operating constraints.

In the embodiment illustrated in FIG. 1, the analyzer system 100 is configured such that the reciprocating motion of the piston 104 is uncoupled from rotation motion of the piston 104, thereby allowing control of the piston 104 in a linear manner. In one embodiment, two motors 106 are provided, one motor 106a to rotate the piston 104 for the valving action, and the other motor 106b to control the linear position of the piston 104 within a piston liner 108 to perform pumping action. This dual motor configuration allows for easy and accurate sub-volume pumping below the normal full cycle volume. In another embodiment, instead of a single part, the valve 110 is provided separate from the piston 104, such that the valve 110 is a distinct piece or component. The piston 104 for the pump 102 is also simplified, with the valve piece acting within the same ceramic liner 108 as the piston 104 in some embodiments. This configuration allows inlet and outlet ports 110, 112 to be closer together in angular position, which reduces the amount of valve rotation travel from 180 degrees to 90 degrees as an example in various embodiments. The reduced operating range decreases the amount of time to position the valve 110, as the valve 110 only has to move between these two positions rather than make a full or half revolution. In addition, the piston 104 only moves linearly in various embodiments, as described herein, such that the mechanical control is also simplified.

Additionally, one or more embodiments may be configured for a larger full cycle volume, such as 500 μL per full cycle instead of 50 μL. The use of a larger cycle volume allows for a slower, more power efficient system, especially with typically encountered low to medium operating flow rates (e.g., 100-200 mL/hour).

The exhaust phase, especially with a larger full cycle volume, can cause a momentary buildup of pressure on the occluded intake side, thereby influencing the operating characteristics of the device under test. This buildup of pressure will vary according to the flow rate of the device under test, but in practice could reach several PSI and therefore also trigger a soft or partial occlusion alarm. By practicing one or more various embodiments, pressure build-up during the exhaust phase is eliminated or reduced, power consumption is further reduced, accuracy improved, and the mechanical linkages are simplified (as compared to conventional fluid metering pumps or alternate embodiments).

In such embodiments, the valve 110 is further uncoupled from the pump 102 by separating the ceramic valve 110 out of the piston liner 108 into a separate liner 116 to reduce the package height and machining complexity. It should be noted that in order to reduce or eliminate the buildup of pressure during the exhaust phase, an additional flat is provided (e.g., machined) on the valve 110 opposite an existing one, such that an additional pump 120 (ceramic piston/liner) is provided 180 degrees out of phase of the pump 102. Thus, in operation, while one pump 102 or 120 is in a dispense (exhaust) phase, the other pump 120 or 102 is in a suction (inlet) phase, and vice-versa. The dual pump design results in much reduced or minimal pressure buildup during valve switching, allowing for a more realistic test of an infusion pump 122. In addition, due to the use of opposite phase pumps, the exhaust phase of one can be accomplished without any need for speed, therefore the power efficiency is greatly improved and allows for the use of smaller motors. Accordingly, in some embodiments, a portable battery-powered configuration of the analyzer system 100 for mobile use is provided. Moreover, linear displacement of the pumps 102, 120 is easily controllable and accurate and the rotary valve 110 only has to turn 90 degrees at every transition point. Various embodiments are also not sensitive to air bubbles, as the analyzer system 100 does not rely on tracking bubbles for testing, and the analyzer system 100 is not position or solution sensitive.

The analyzer system 100 provides a more rugged pressure sensor. For example, conventional infusion pump analyzers use a pressure sensor to monitor the pressure that is generated by the infusion pump. Most analyzers use a sensor that is not ideal for fluid applications, that is, the sensor typically used is configured for use in an application involving gases. In addition, the sensors are easily damaged when saline buffer solutions evaporate, forming a dried salt blockage.

The analyzer system 100 in various embodiments includes a pressure sensor 124 with a stainless steel oil-filled diaphragm that isolates and protects the pressure sensor 124 from the media. In various embodiments, the pressure sensor 124 is mounted such that fluid flows across the wide surface of the pressure sensor 124 rather than dead-ending at the pressure sensor 124. This configuration for the pressure sensor 124 provides a more rugged design with many years of service life, even when its users test with saline buffer solutions instead of water.

In some embodiments, the pressure sensor 124 is located between the infusion pump 122 and inlet to the flow engine to determine when the incoming flow is present. As the infusion pump 122 dispenses fluid into the analyzer system 100, the pressure rises. The flow engine moves the piston(s) 108 at a rate to maintain the pressure to a pre-programmed amount. Accordingly, the target pressure is adjustable. For example, the ANSI/AAMI ID26:2004/(R)2009 standard requires infusion pumps to operate with a user-selectable back pressure from −100 to +300 mmHg, which can be accomplished using one or more embodiments. For other conventional technologies (including the electronic burette and bubble tracking systems) this is not possible without additional external equipment.

The analyzer system 100 can perform occlusion testing by positioning the rotary valve 110 in an intermediate position such that the flow path from the infusion pump 122 to the analyzer system 100 is occluded. In operation, the pressure sensor 124 monitors the occlusion pressure of the infusion pump 122 and allows for easy verification of the safety features of the infusion pump 122 including, for example, alarms, auto-reverse, as well as measuring the bolus volume (volume built up during the expansion of the administration set) after the occlusion is cleared.

The analyzer system 100 has a modular design as described herein and in various embodiments all calibration and control is self-contained in the module. This allows for some embodiments to include a base station with interchangeable modules. In various embodiments, a user-serviceable module may be provided that can be swapped out or switched out for calibration or other service needs, in contrast to a closed-box system in which the entire mainframe has to be sent in for maintenance or repair (e.g., if any of the four channels needs to be serviced/calibrated).

Thus, it should be noted that in some embodiments of the analyzer system 100, plural modules may be provided within the analyzer system 100 to allow multiple infusion pumps 122 to be connected thereto for testing.

In some embodiments, the analyzer system 100 includes a controller 126 that is configured to control operation of the various components (such as shown in box 128) to allow for testing of the infusion pump 122. It should be noted that any type of communicative or operative coupling may be used, between the controller 126 and various components. The controller 126, for example, allows for programmable control of the flow characteristics or properties of the analyzer system 100 by controlling the components 128. However, as should be appreciated, the controller 126 may control different components and may control the components individually, together or in sub-sets or sub-groups.

The analyzer system 100 may also include a processor 128 coupled to the controller 126. The processor 128 can control the operation of the controller 126 to perform certain tests or validations of the infusion pump 122 coupled with the analyzer system 100. The processor 112 is also configured in various embodiments to process received information (such as measurement information from the sensor 124) to determine one or more operating characteristics or parameters of the infusion pump 122. The received information may be stored, for example, in a memory 130, which may also include programming or instructions for controlling the processor 128 to perform one or more operations herein to thereby transform the processor 128 into a specialized processor. Additionally, the processor 128 may be configured to control the analyzer system 100 to provide, automatic, semi-automatic or manual control and operation.

It should be noted that the memory 130, which may be any type of electronic storage device, can be coupled to the processor 128 (or form part of the processor 128). The processor 128 may access the memory 130 to obtain stored information as described herein.

While FIG. 1 illustrates a particular connection arrangement of the various components, a skilled artisan would appreciate that other connection arrangements may be made that are within the scope of this disclosure. Additionally, the various components may be housed within the same or different physical units and the separation of components within FIG. 1 is merely for illustration.

The analyzer system 100 can also comprise other components, such as one or more communication subsystems to allow communication with external devices, such as networks, printers, etc. that are not coupled with analyzer system 100. Thus, additional components may form part of or communicate with the analyzer system 100.

In some embodiments, the analyzer system 100 may be embodied as a test device or as part of a test device, which may be contained within a housing 160 as shown in FIGS. 6-9. The housing may be formed as a two-piece design having a top shell 162 and a bottom shell 164 with a display support 166 movably mounted to the top shell 162. For example, the display support 166 may be pivotally mounted to the top shell 162 to allow positioning of a display (not shown) coupled thereto at different angles, which may be predefined angular locations (based on the positioning of detents) or may be variably positionable in other embodiments. Different operational angles are shown in FIGS. 6-9.

Figure 2:
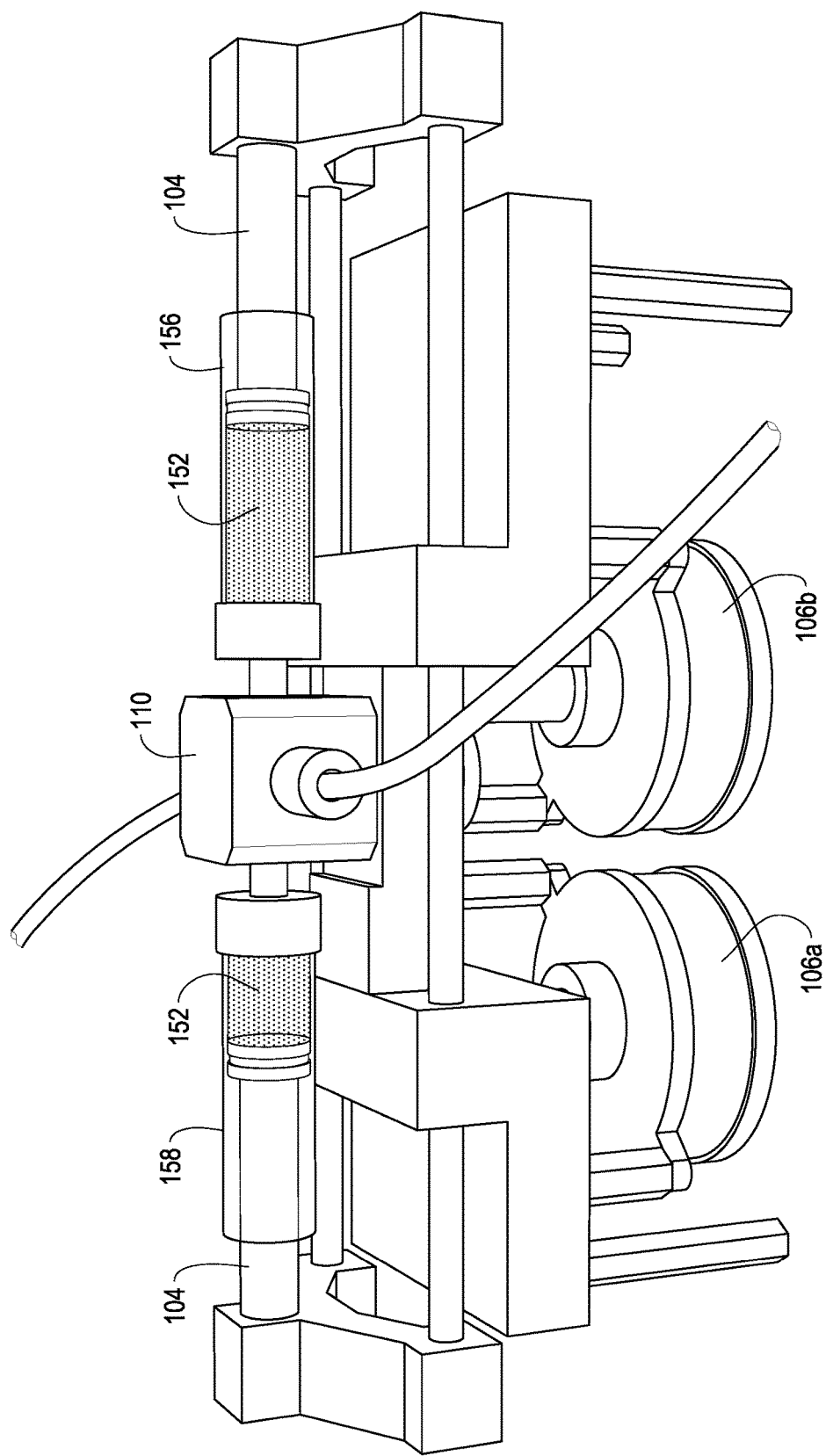
FIG. 2 is diagram showing components of an analyzer system for testing an infusion pump in accordance with an embodiment.
Figure 3:
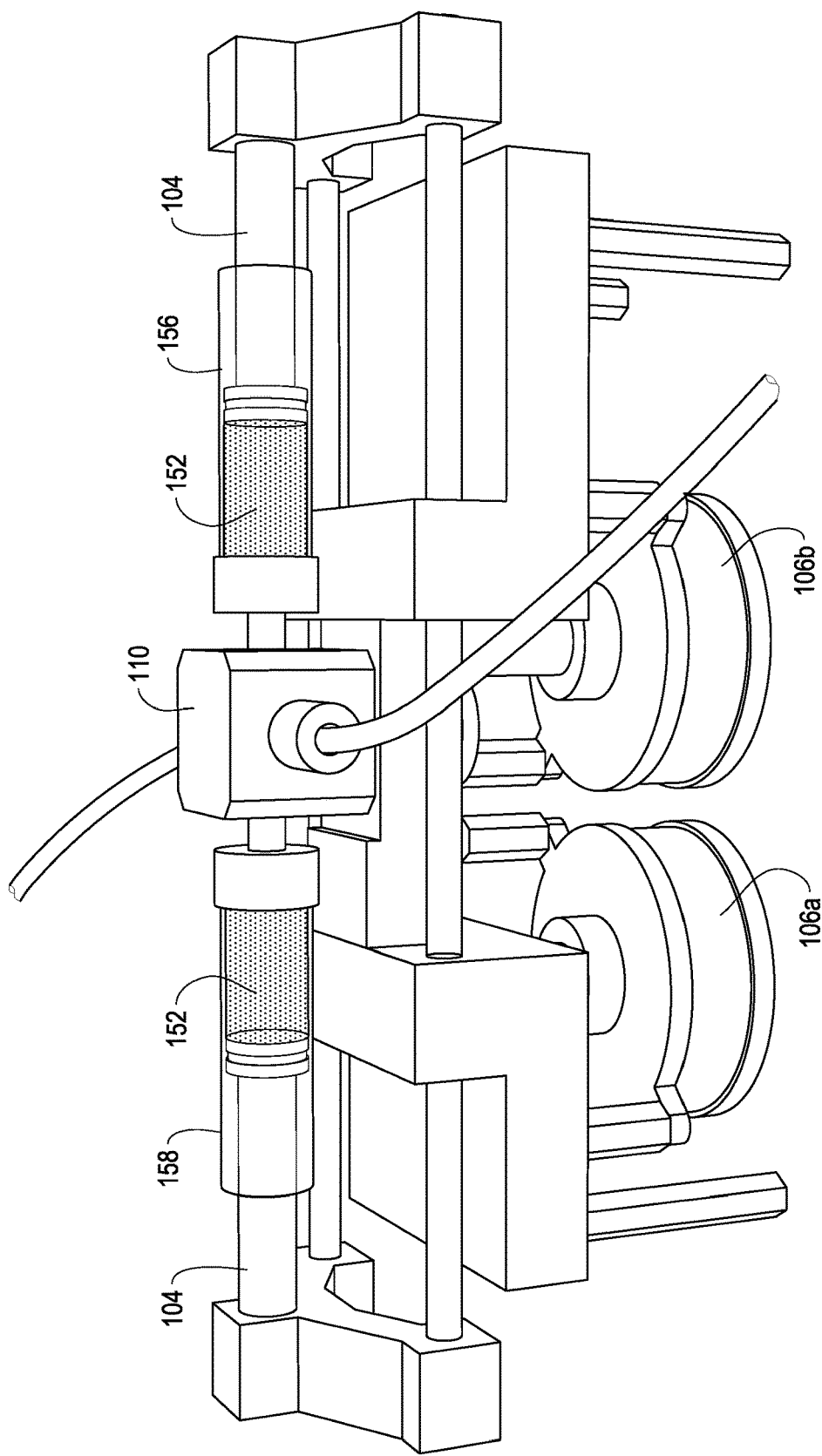
FIG. 3 is another diagram showing components of an analyzer system for testing an infusion pump in accordance with an embodiment.
Figure 4:
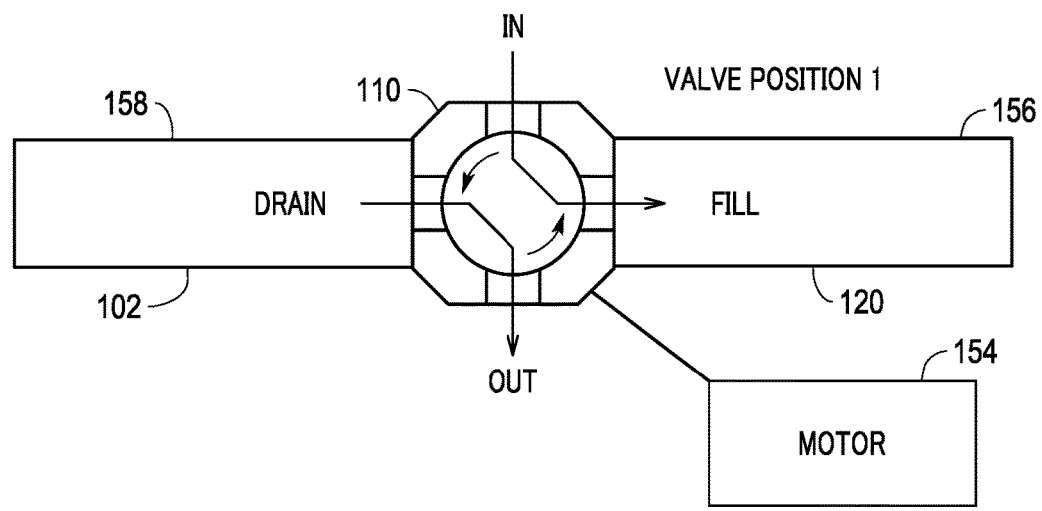
FIGS. 4 and 5 illustrate pumping operation in accordance with various embodiments.
Figure 5:
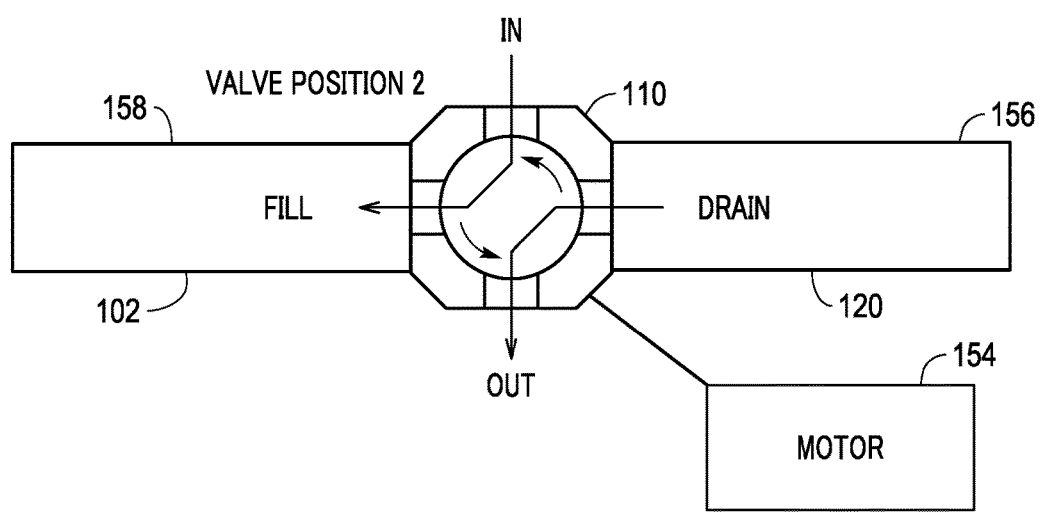
Figure 6:
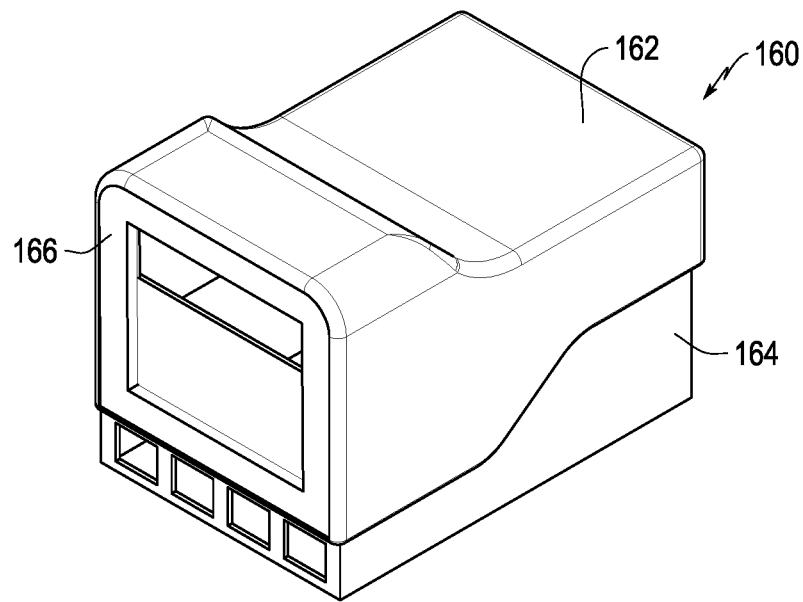
FIGS. 6-9 illustrate a housing for an analyzer system in accordance with one embodiment.
Figure 7:
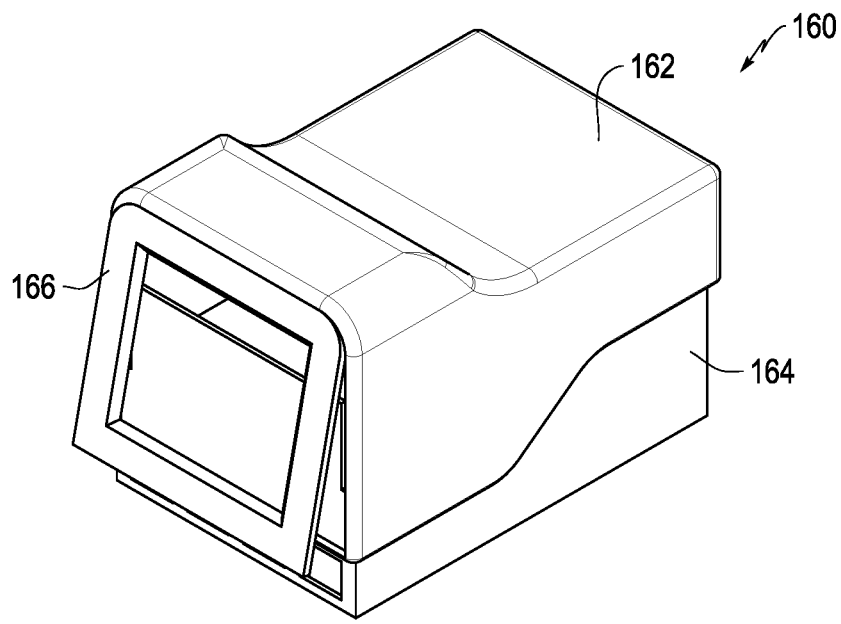
Figure 8:
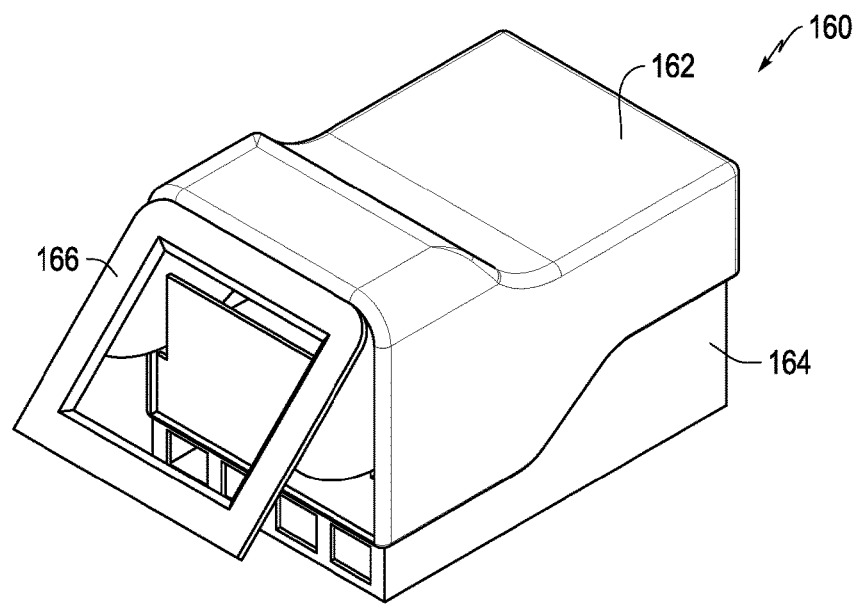
Figure 9:
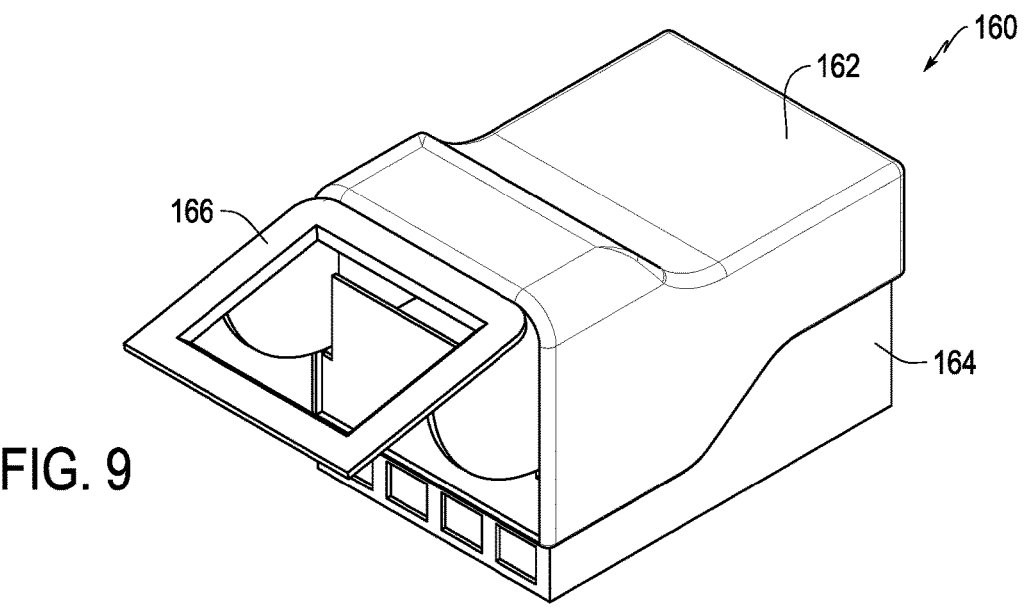
Figure 10:
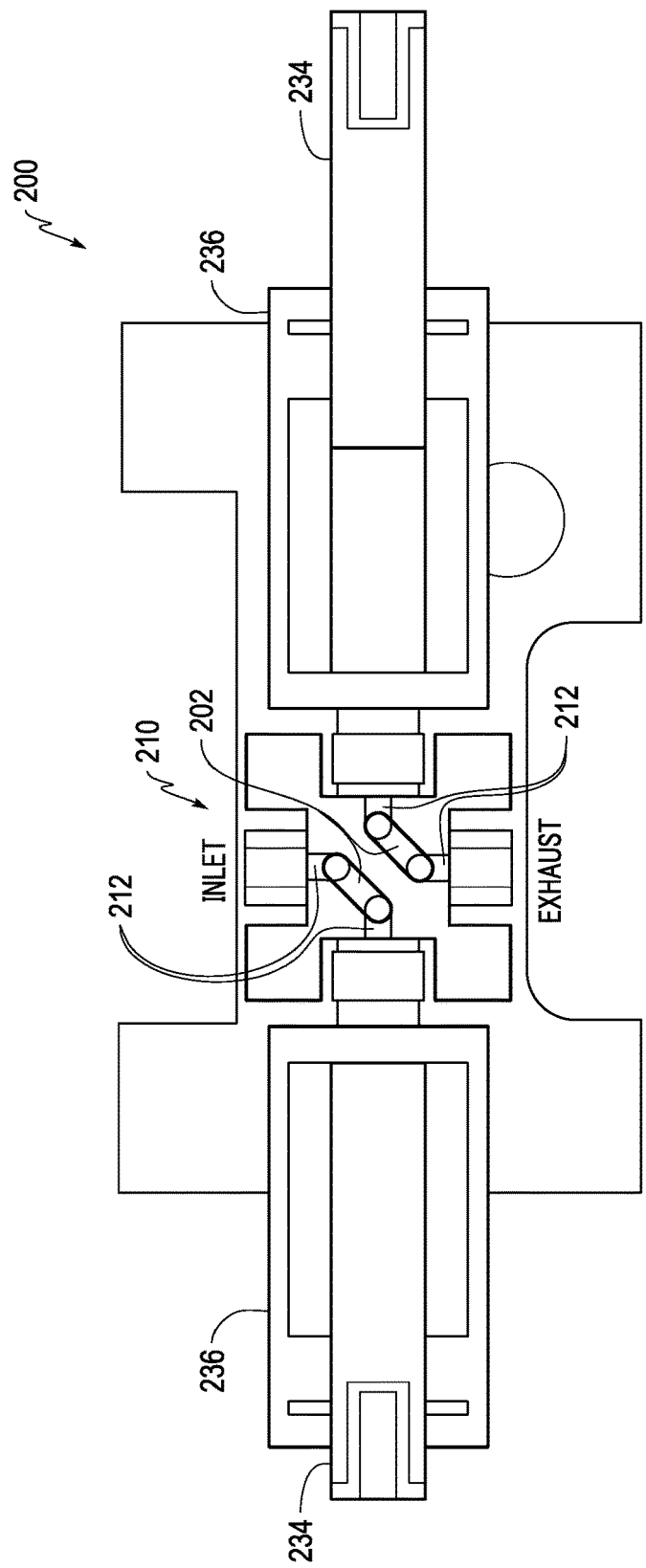
FIGS. 10-16 illustrate an analyzer system in accordance with another embodiment.
Figure 11:
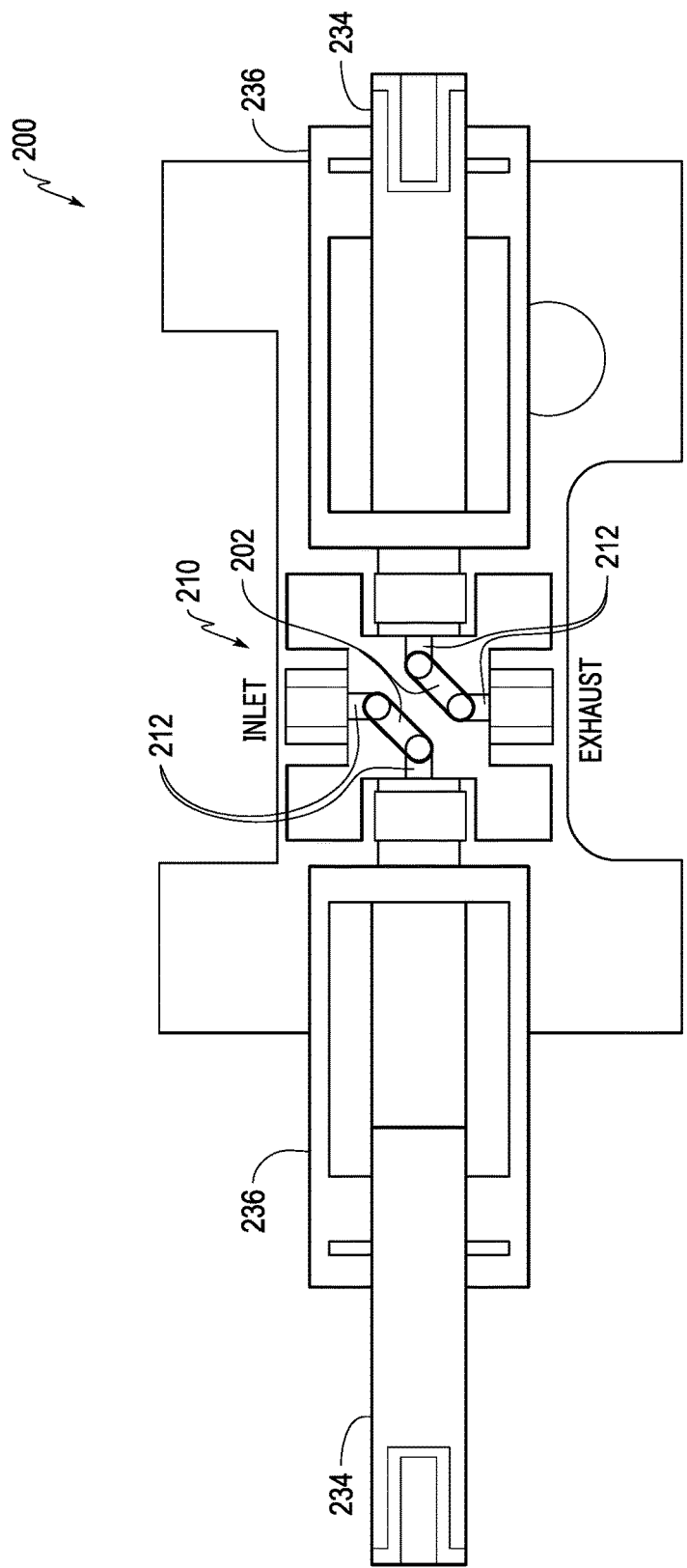
Figure 12:
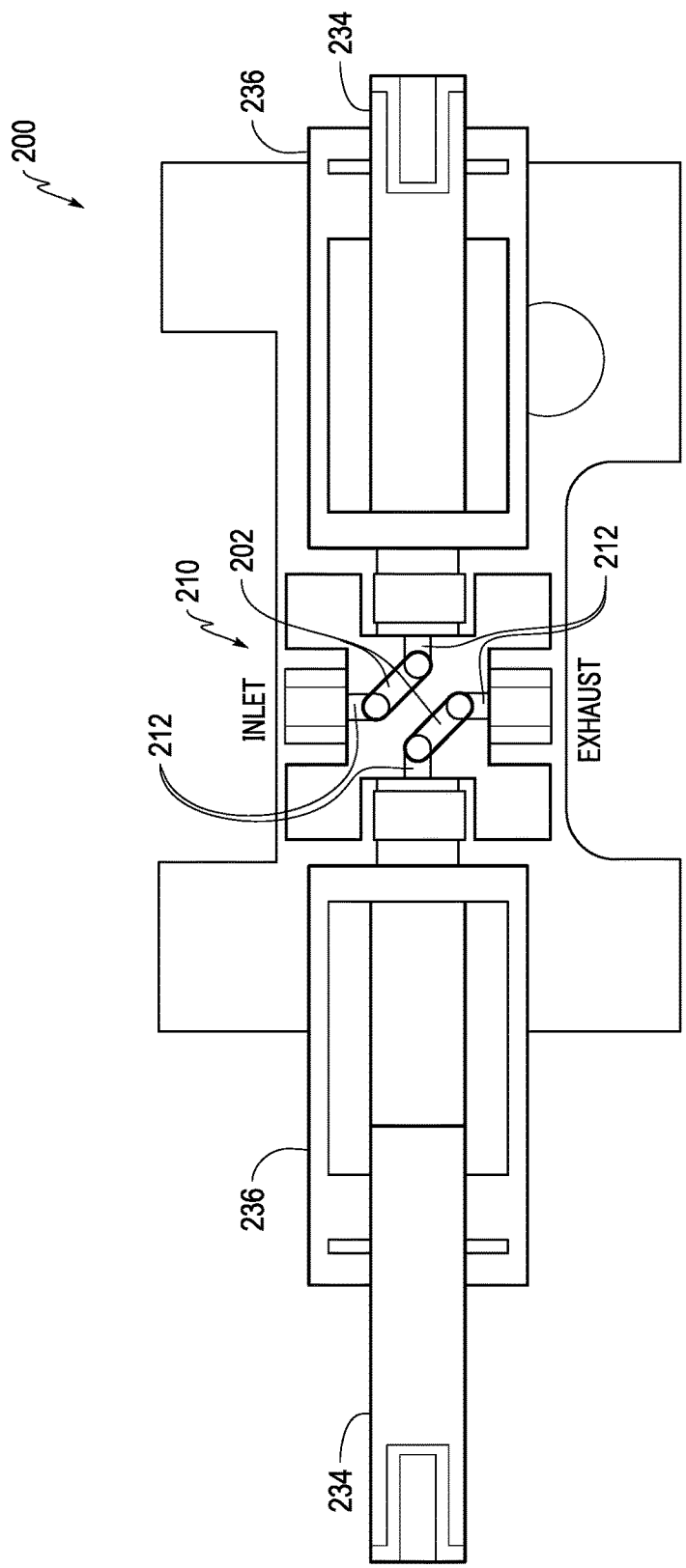
Figure 13:
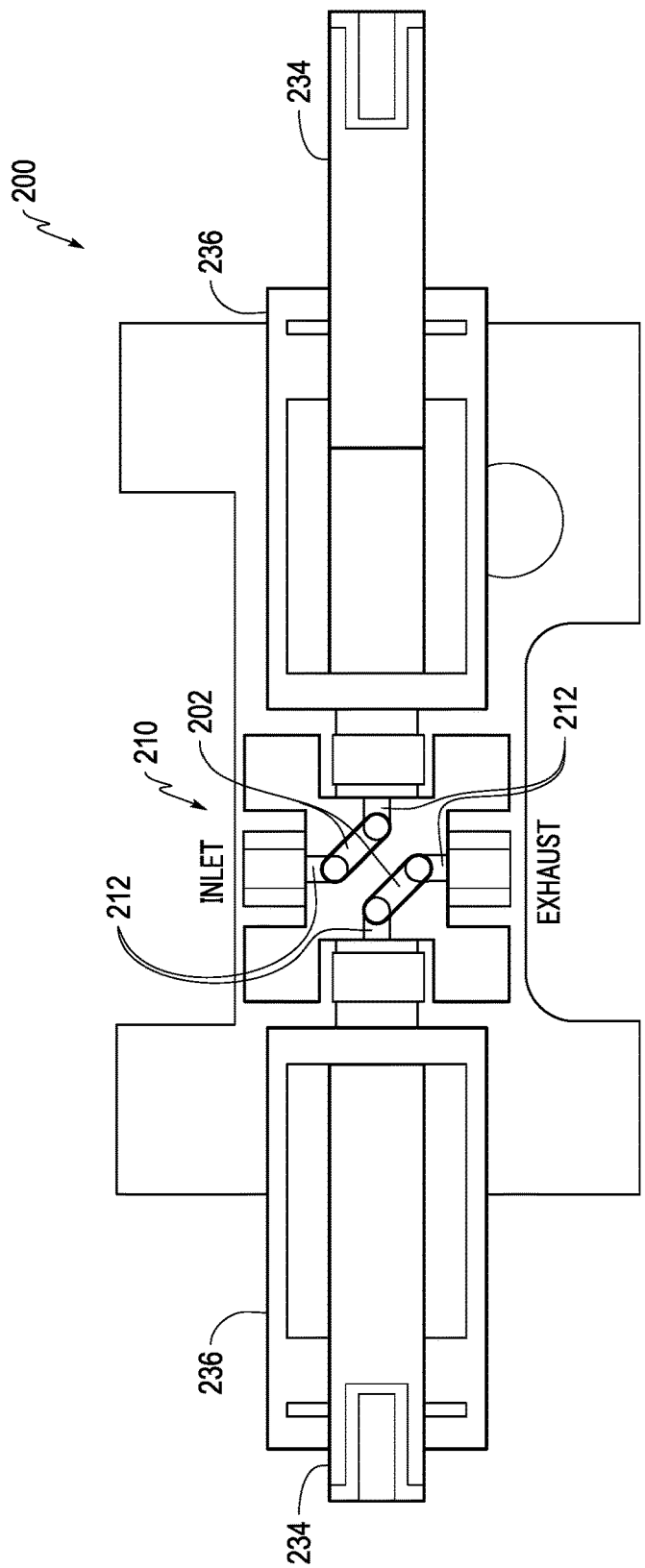
Figure 14:
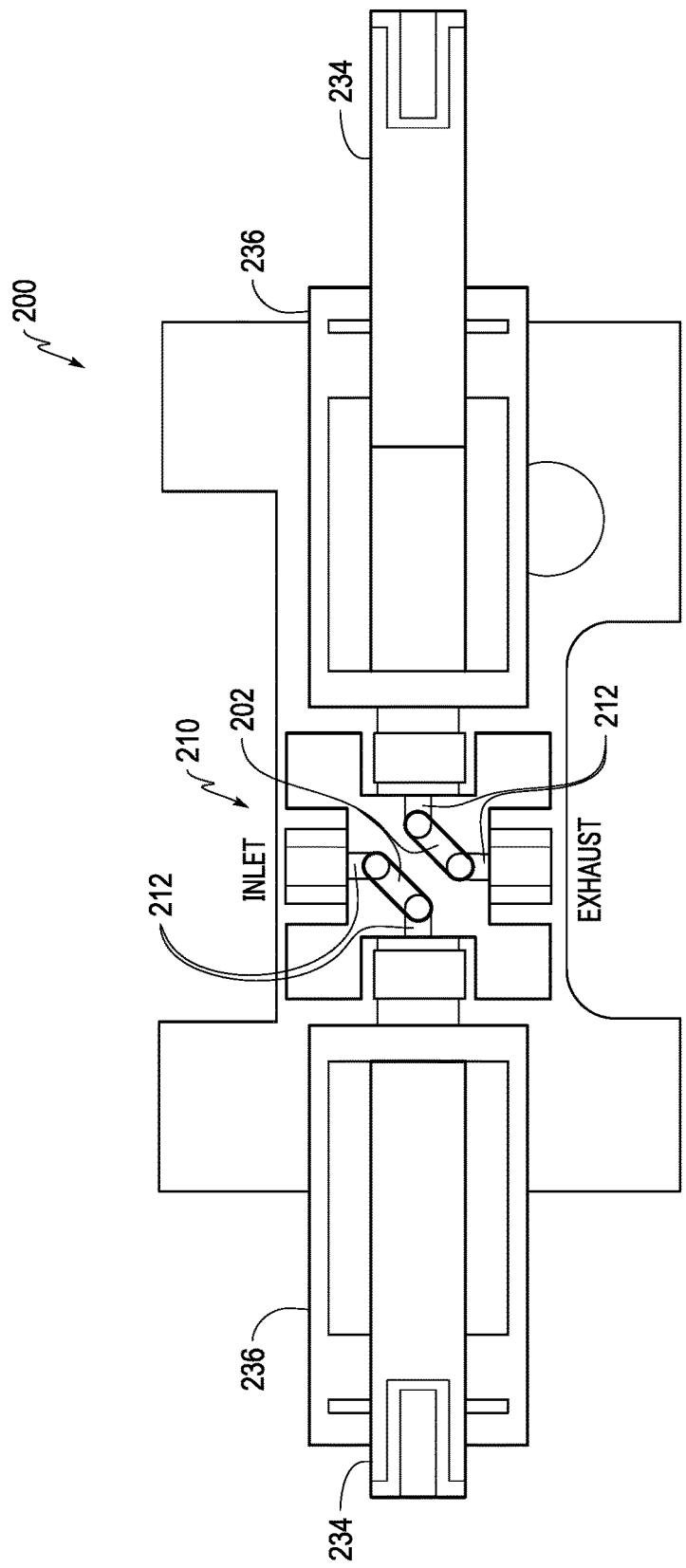
Figure 15:
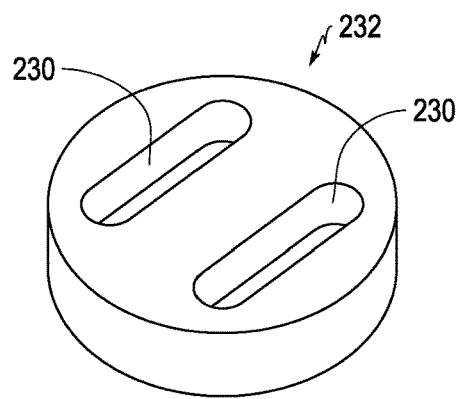

The analyzer system 100 may be configured to have a linear operating configuration such as shown in FIGS. 2 and 3. As can be seen, the motors are separate components allowing for independent operation or control of different functions, such as valving and pumping of fluid 152. For example, in operation, and as shown in FIGS. 4 and 5, the valve 110 may be mounted at the center of two linear piston pumps 102 and 120 (in various embodiments operating similar to how syringes operate). The valve 110 has two "flats" machined in it, 180 degrees apart on the outside diameter, and the valve stem is actuated by the motor 106b. The linear piston pumps 102 and 120 are linked mechanically together such that only one motor 106a is needed to move both pistons simultaneously. It should be noted that the aforementioned linear piston pumps can be comprised of several materials such as ceramic, metal, plastic, or glass (or other materials) and that the pistons may or may not have a secondary seal. As an example, two glass syringes could be used as the linear piston pumps in combination with the valve. As should be appreciated, the combination of the valve and dual linear piston pumps allows for one cylinder 156 to be filling at the same time that the other cylinder 158 is draining. This operation in various embodiments creates an almost continuous flow rate through analyzer system 100. It should be noted that a fixed volume of fluid may be filled into the cylinder 156 or 158, which is then drained.

Variations and modifications are contemplated. For example, for measurement systems that use a stepper motor for fine volume control, an open-loop position feedback design is used. Open-Loop position control can result in cumulative errors in volume measurement accuracy unless periodically corrected. In the analyzer system 100, for additional accuracy, an encoder (either linear or rotary) may be provided for closed-loop positional control over linear volume of the flow engine, enhancing system accuracy. Even with open-loop control, the analyzer system 100 is inherently more accurate due to the linear volume per motor step versus the sinusoidal volume of conventional and/or known fluid metering designs.

Following are example operating performance characteristics and features that may be achieved with of one or more embodiments of the analyzer system 100 (however, as should be appreciated, different operating performance characteristics and features are possible and encompassed within the present disclosure):

embodiments, a single motor is coupled to the dual linear piston pumps and a single motor is coupled to the valve. The dual linear piston pumps and the valve are configured in various embodiments to uncouple valving and pumping operations.

Variations and modifications are contemplated. For example, FIGS. 10-16 illustrate an analyzer system 200 in accordance with some embodiments that allows for measur-

|  | Parameter | IPA-3200 (proposed) | IPA-3400 (proposed) |
|---|---|---|---|
| Flow Measurement | Flow Rate (ml/hr) | 0.01-1600 | 0.01-1600 |
|  | Flow Resolution (ml/hr) | 0.001 (1.0 µL) | 0.001 (1.0 µL) |
|  | Accuracy | 1% rdg after 100 µl | 1% rdg after 100 µl |
|  | Min Volume (ml) | 0.05 (50 µL) | 0.05 (50 µL) |
|  | Channels | 1 | 1, 2, 3 or 4 (user-installable) |
| Volume Measurement | Volume Range (mL) | 0 to 9999 | 0 to 9999 |
|  | Volume Resolution (mL) | 0.001 (1.0 µL) | 0.001 (1.0 µL) |
|  | Min Bolus Volume (mL) | 0.01 (10 µL) | 0.01 (10 µL) |
|  | Volume Accuracy | 1% rdg after 100 µl | 1% rdg after 100 µl |
| Elapsed Time | Range | 0-120 Hours | 0-120 Hours |
|  | Resolution | 1 Second | 1 Second |
|  | Accuracy | 0.5 Second | 0.5 Second |
| Occlusion (Pressure) Test | Range | −258.57-2585.75 mmHg (−5-50 PSI) | −258.57-2585.75 mmHg (−5-50 PSI) |
|  | Resolution | 0.05 mmHg (0.001 PSI) | 0.05 mmHg (0.001 PSI) |
|  | Accuracy | 0.25% FS | 0.1% FS |
| Back-Pressure Control | Range | −200-600 mmHg (−3.867-11.602 PSI) | −200-600 mmHg (−3.867-11.602 PSI) |
|  | Resolution | 0.05 mmHg (0.001 PSI) | 0.05 mmHg (0.001 PSI) |
|  | Accuracy | 0.25% FS | 0.1% FS |
| Interface | Fluid Fittings | Luer | Luer |
|  | Barcode Reader Supported | Yes | Yes |
|  | Keyboard Supported | Yes | Yes |
|  | Printer Port | No | Yes |
|  | Nurse Call | No | Yes with Optional External Module |
|  | PCA trigger output |  |  |
|  | Communication | USB, Bluetooth | USB, Bluetooth |
|  | Display | 5" Touch-screen | 7" Touch-screen |
|  | Other | Mass Storage support for external USB flash drive | Mass Storage support for external USB flash drive |
| Power Supply | Battery | Yes - Rechargeable Lithium | No |
|  | Voltage | Charger Input 90-265 VAC 50/60 Hz | Input - 90 to 264 VAC, 50/60 Hz |
| User Interface | Graph mode? | No | Yes |
|  | PC Software Graph mode? | Yes | Yes |
|  | Weight | <5 lbs | 1 chan < 8 Lbs 2 chan < 10 lbs 3 chan < 12 lbs 4 chan < 14 lbs |
|  | Size (H × W × D) | 10 × 5.5 × 6 Inches | 7.8 × 10 × 8.5 Inches |
|  | Operating Temperature | 15 to 40° C. | 15 to 40° C. |
|  | Data Storage | Internal 8 GB microSD card | Internal 32 GB microSD card |

In various embodiments the IPA-3200 is a handheld system and the IPA-3400 is a bench top or desktop system.

In some embodiments, the analyzer system 100 allows for measuring different operating characteristics of the infusion pump 122, which testing conditions or parameters may be programmable as discussed herein.

Thus, one or more embodiments provide an infusion pump analyzer that includes (i) a fluid flow path configured to be coupled to an infusion pump to be tested, (ii) a pair of fluid chambers, (iii) dual linear piston pumps coupled with the pair of fluid chambers and the fluid flow path to control the flow of fluid therethrough and (iv) a valve coupled with the pair of fluid chambers and configured to rotate 90 degrees to selectively fill and drain the pair of fluid chambers. The valve may include two flats or passageways that define the rotation of 90 degrees. Additionally, in various ing different operating characteristics of the infusion pump 122 (shown in FIG. 1), which testing conditions or parameters may be programmable as discussed herein.

In the analyzer system 200, a valve 210 is coupled with a pair of fluid chambers and configured to selectively fill and drain the pair of fluid chambers. The valve 210 includes two passageways 202 that replace the two flats that are implemented in the analyzer system 100. The passageways 202 are formed from slots 230 (or grooves) in a rotor 232, illustrated as a disc in FIG. 15. The slots 230 are configured to align with openings 212 in the valve 210. In operation, the valve 210 is operated similar to the valve 110 with a sensor used in various embodiments to detect the correct position of the valve 210 (e.g., alignment of the passageways 202) before linear motion is started.

For example, in operation, once alignment is detected, linear motion is started to drain one fluid chamber and fill the other fluid chamber (step 1), then linear motion is stopped (step 2) when the draining and filling (exhaust and intake phases) are completed. A valve cycle is then performed that causes the rotor 232 to rotate (step 3) to align the passageways 202 with a different respective pair of openings 212 (e.g., 90 degree rotation). The valve cycle is then stopped, such that rotation of the rotor 232 is stopped. Then, linear motion is again performed (step 4), but in the reverse or opposite direction of the first linear motion, which caused filling and draining of the fluid chambers that were drained and filled, respectively, in the first linear motion operation. Then, the rotor 232 is again rotated (step 5), either in the same direction of in the reverse or opposite direction from the first rotation operation. This operation (steps 1-5) are illustrated in FIGS. 10-14 that shows different suction and exhaust strokes of a pair of pistons 234 of each of a pair of cylinders 236 that is controlled in combination with the rotation of the rotor 232. It should be noted that the operation of the various components, including, for example, the motion thereof, in the analyzer system 200 is similar to the operation of the analyzer system 100. It also should be noted that the pistons 234 in various embodiments are mechanically coupled or linked together.

Figure 16:
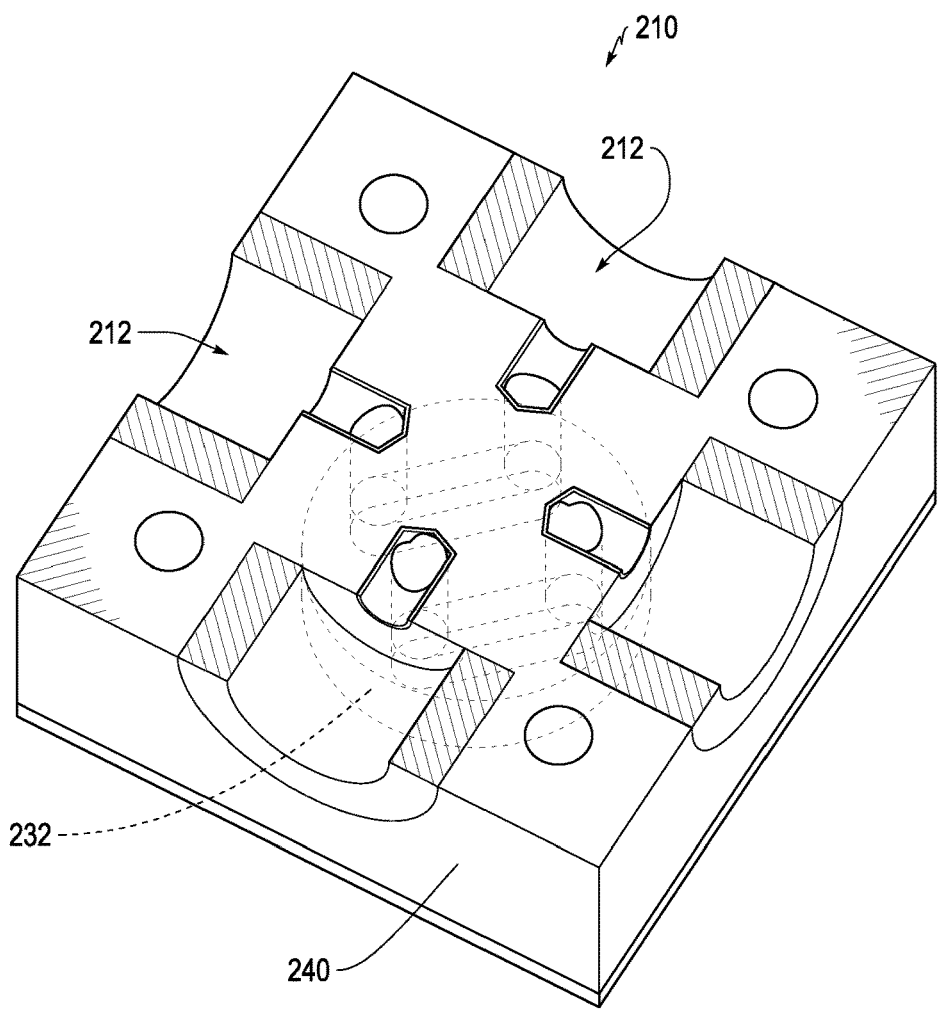
Figure 17C:
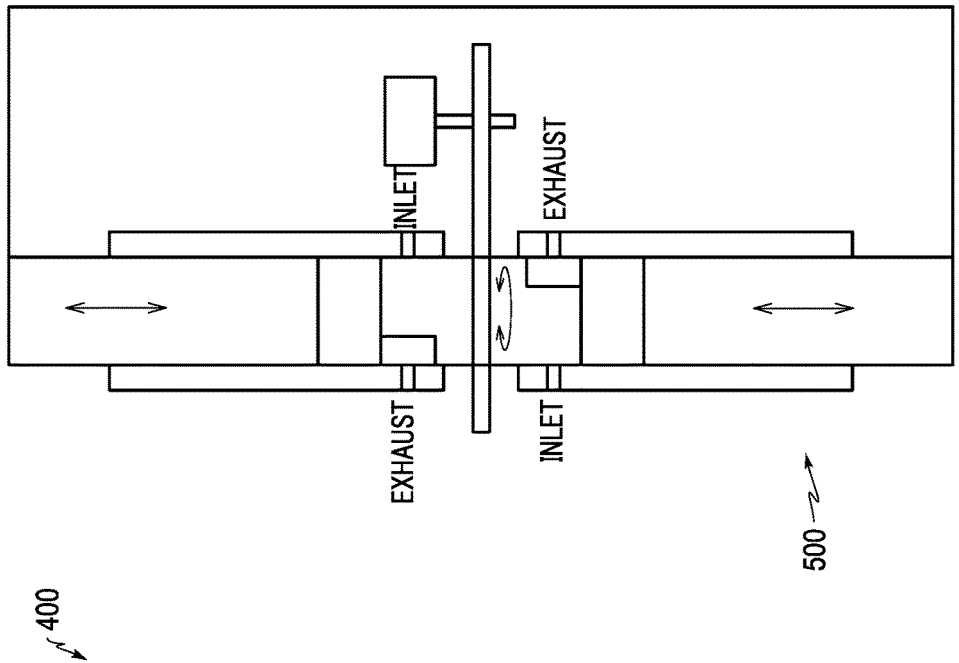
Figure 17B:
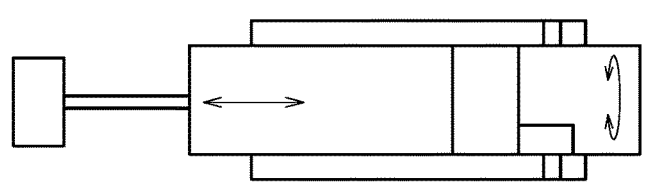
Figure 17A:
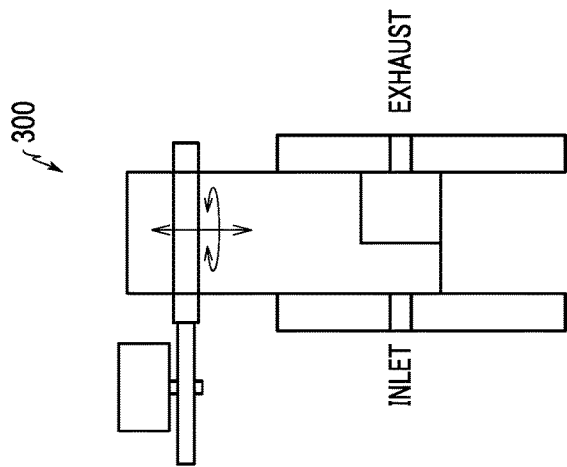

FIG. 16 illustrates a stator 240 of the analyzer system 200. In various embodiments, direct acting ceramics are used. For example, in some embodiments, a direct acting spring is provided to bias the various components, such as within the stator 240, such that no seals are used. Thus, in some embodiments, the stator 240 is a ceramic stator with a port formed (e.g., drilled) in each side to define the openings 212 (e.g., ports), with four holes formed within the stator 240 (in the top/bottom direction) that define the passageways 202. The ports and holes may have different configurations, sizes and/or shapes as desired or needed.

FIGS. 17A-17E illustrate different embodiments of pump configurations for analyzer systems, including pump configurations 600 and 700 for the pump the analyzer system 100 and the analyzer system 200, respectively. The pump configurations 600 and 700 are configured as fluid metering pumps having dual fluid chambers, with the pump configuration 600 having the two flat design valve and the pump configuration 700 having the rotor/stator valve design. The pump configuration 300 illustrates a fluid metering pump with separate actuators and the pump configuration 400 illustrates a fluid metering pump with separate piston/valve and actuators. The pump configuration 500 illustrates a fluid metering pump with dual fluid chambers and a single integrated valve. It should be noted that features of one or more of the pump configurations 300-700 may be combined or separated as desired or needed.

It should be noted that the various embodiments may be implemented in hardware, software or a combination thereof. The various embodiments and/or components, for example, the modules, or components and controllers therein, also may be implemented as part of one or more computers or processors or FPGAs. The computer or processor or FPGA may include a computing device, an input device, a display unit and an interface, for example, for accessing the Internet. The computer or processor may include a microprocessor. The microprocessor may be connected to a communication bus. The computer or processor may utilize external communications such as RS-232, Bluetooth, USB, or Ethernet, among others. The computer or processor or FPGA may also include a memory. The memory may include Random Access Memory (RAM) and Read Only Memory (ROM). The computer or processor or FPGA further may include a storage device, which may be a hard disk drive or a removable storage drive such as a floppy disk drive, optical disk drive, and the like. The storage device may also be other similar means for loading computer programs or other instructions into the computer or processor.

As used herein, the terms "system," "circuit," "component," or "module" may include a hardware and/or software system that operates to perform one or more functions. For example, a module, circuit, component, or system may include a computer processor, controller, or other logic-based device that performs operations based on instructions stored on a tangible and non-transitory computer readable storage medium, such as a computer memory. Alternatively, a module, circuit, component, or system may include a hard-wired device that performs operations based on hard-wired logic of the device. The modules or circuits or components shown in the attached figures may represent the hardware that operates based on software or hard-wired instructions, the software that directs hardware to perform the operations, or a combination thereof.

The block diagrams of embodiments herein illustrate various blocks labeled "circuit" or "module." It is to be understood that the circuits or modules may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

It is to be understood that the above description is intended to be illustrative, and not restrictive. For example, the above-described embodiments (and/or aspects thereof)

may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) paragraph, unless and until such claim limitations expressly use the phrase "means for" followed by a statement of function void of further structure.

What is claimed is:

1. An infusion pump analyzer comprising:
 a fluid flow path configured to be coupled to an infusion pump to be tested;
 a pair of fluid chambers;
 dual linear piston pumps coupled with the pair of fluid chambers and the fluid flow path to control the flow of fluid therethrough; and
 a valve coupled with the pair of fluid chambers and configured to rotate to selectively fill and drain the pair of fluid chambers.

2. The infusion pump analyzer of claim 1, wherein the valve comprises a stator and rotor that define the rotation, the rotor configured as a disc having two slots formed therein defining two passageways.

3. The infusion pump analyzer of claim 2, wherein the stator comprises a ceramic stator having no seals therein.

4. The infusion pump analyzer of claim 1, wherein the valve comprises two flats that define the rotation.

5. The infusion pump analyzer of claim 1, wherein the valve is configured to rotate 90 degrees.

6. The infusion pump analyzer of claim 1, further comprising a single motor coupled to the dual linear piston pumps and a single motor coupled to the valve.

7. The infusion pump analyzer of claim 1, wherein the dual linear piston pumps and the valve are configured to uncouple valving and pumping operations.

8. The infusion pump analyzer of claim 1, further comprising a pressure sensor within the fluid flow path such that fluid flows across a wide surface of the pressure sensor.

9. The infusion pump analyzer of claim 1, wherein the valve is configured to control fluid flow such that one of the pair of fluid chambers is filling while the other one of the pair of fluid chambers is draining.

10. The infusion pump analyzer of claim 1, wherein the dual linear piston pumps comprise a pair of pistons that are mechanically coupled to each other.

11. A method of controlling fluid metering for an infusion pump analyzer, the method comprising:
 starting linear motion of dual linear pistons in a first linear direction to drain one fluid chamber and fill another fluid chamber through passageways aligned with openings in a valve;
 stopping linear motion of the dual linear pumps when the draining and filling that define exhaust and intake phases, respectively, are completed;
 performing a valve cycle that causes a portion of the valve to rotate in a first direction to align the passageways with a different respective pair of openings;
 stopping the valve cycle, such that rotation of the valve is stopped;
 starting linear motion of the dual linear pistons in a second linear direction, the second linear direction being opposite to the first linear direction that caused filling and draining of the fluid chambers that were drained and filled, respectively, when the dual linear pistons were moved in the first linear direction;
 stopping linear motion of the dual linear pumps when the draining and filling that define exhaust and intake phases, respectively, are completed;
 performing a valve cycle that causes a portion of the valve to rotate in a second direction to align the passageways with a different respective pair of openings, the second direction being either the same or opposite to the first direction; and
 stopping the valve cycle, such that rotation of the valve is stopped.

* * * * *